United States Patent
Raneburger et al.

(10) Patent No.: US 6,440,462 B1
(45) Date of Patent: Aug. 27, 2002

(54) AGGLOMERATES OF β-LACTAM ANTIBIOTICS AND PROCESSESS FOR MAKING AGGLOMERATES

(75) Inventors: Johannes Raneburger, Woergl; Erich Zeisl, Jenbach, both of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/142,183

(22) PCT Filed: Mar. 13, 1997

(86) PCT No.: PCT/EP97/01269

§ 371 (c)(1),
(2), (4) Date: Sep. 2, 1998

(87) PCT Pub. No.: WO97/33564

PCT Pub. Date: Sep. 18, 1997

(30) Foreign Application Priority Data

Mar. 13, 1996 (AT) .................................................. 474/96
Aug. 12, 1996 (AT) .................................................. 1445/96

(51) Int. Cl.⁷ .............................. A61K 9/16; A61K 9/14
(52) U.S. Cl. ....................... 424/489; 424/499; 424/500; 424/501; 424/502; 424/464; 424/465; 514/951
(58) Field of Search ................................ 424/489, 499, 424/500, 501, 502, 464, 408, 465; 514/951

(56) References Cited

U.S. PATENT DOCUMENTS

| | | | |
|---|---|---|---|
| 3,551,457 A | 12/1970 | Ross .................... | 260/345.5 |
| 4,143,129 A | * 3/1979 | Marsden | |
| 4,301,149 A | 11/1981 | Crowley ..................... | 424/114 |
| 4,441,609 A | 4/1984 | Crowley ..................... | 206/204 |
| 4,795,646 A | 1/1989 | Schlünken .................. | 424/489 |
| 5,160,469 A | 11/1992 | Moest et al. ................. | 264/117 |
| 5,191,114 A | 3/1993 | Chen ......................... | 562/496 |
| 5,288,861 A | * 2/1994 | Clark et al. | |
| 5,300,303 A | 4/1994 | Grimmer et al. ............ | 424/489 |
| 5,453,280 A | 9/1995 | Moest et al. ................. | 424/458 |
| 5,514,383 A | 5/1996 | Laly et al. .................. | 424/464 |
| 5,686,632 A | 11/1997 | Walsh ........................ | 549/410 |
| 5,705,192 A | 1/1998 | Bethge et al. .............. | 424/489 |
| 5,869,101 A | 2/1999 | Möller ....................... | 424/489 |
| 5,948,422 A | * 9/1999 | Van Koutrik et al. | |

FOREIGN PATENT DOCUMENTS

| | | |
|---|---|---|
| BE | 832097 | 2/1976 |
| BE | 870988 | 4/1979 |
| DE | 3636209 A1 | 4/1988 |
| DE | 3712058 A1 | 10/1988 |
| DE | 3929864 A1 | 3/1991 |
| DE | 4014262 A1 | 11/1991 |
| DE | 4231493 A1 | 3/1994 |
| EP | 0080862 | 6/1983 |
| EP | 0194880 A | 9/1986 |
| EP | 0281200 | 9/1988 |
| EP | 0396335 | 11/1990 |
| EP | 0414115 A | 2/1991 |
| EP | 0733363 A1 | 9/1996 |
| FR | 2282258 | 3/1976 |
| GB | 1166958 | 10/1969 |
| GB | 2187952 A | 9/1987 |
| WO | 92/08463 | 5/1992 |
| WO | 92/19227 | 11/1992 |
| WO | 94/23700 | * 10/1994 |
| WO | 94/27557 | 12/1994 |
| WO | 95/20382 | 8/1995 |
| WO | 95/24890 | 9/1995 |
| WO | 9528927 A | 11/1995 |
| WO | 96/04908 | 2/1996 |
| WO | 96/24337 | 8/1996 |

OTHER PUBLICATIONS

Chemical Abstracts 104:28430e, Sato et al., Jpn. J. Antibiot., vol. 38(2) pp. 327–41 (1985).
Chemical Abstracts 104:28431f, Iwai et al., Jpn. J. Antibiot., vol. 38(2), pp. 342–58 (1985).
Chemical Abstracts, vol. 120, No. 24, Abstract No. 307152, XP002034322, Jun. 13, 1994.
H. Leuenberger, Moist Agglomeration of Pharmaceutical Powders (Size Enlargement of Particulate Material)–The Production of Granules by Moist Agglomeration of Powders in Mixers/Kneaders), Handbook Powder Technol., vol. 9, 1994, pp. 377–389.
Chemical Abstracts, vol. 110, No. 8, Abstract No. 63639, XP00203423, Feb. 20, 1989.
Kristensen, H.G., "Agglomeration of Powders", Acta Pharm. Suec., vol. 25, No. 4–5, 1988, pp. 187–204.
Chemical Abstracts, vol. 124, No. 20, Abstract No. 270288, XP002034324, May 13, 1996.
Chow et al., "A Study of the Mechanism of Wet Spherical Agglomeration of Pharmaceutical Powders", Drug Dev. Ind. Pharm., vol. 22, No. 3, 1996 pp. 357–371.
J. Browning, Chemical Engineering, Agglomeration: Growing Larger in Application and Technology, pp 147–169, Dec. 1967.*
Bausch et al., Wet Spherical Agglomeration of Proteins as a New Method to Prepare Parenteral Fast Soluble Dosage Forms, International Journal of Pharmaceutics, 101 pp 63–70, 1994.*
Pharm Res. 10 (10), pp. 1516–1520, 1993.
Boll. Chim. Farm 134 (8), pp. 448–453, 1995.
South Afr. med j. 62 (5 Spec No), pp. 8A to 11A.
Jpn J Antibiot. 36(3), pp. 500–508, 1983.
Antimicrobial Agents Chemother 25 (2), pp. 276–278.
Genitourin Med 62(2), pp., 82–85, 1986.
Drugs 31 (Suppl 3), pp. 113–114, 1986.
Int J Dermatol 32 (3), pp. 218–220, 1993.
J Int med Rcs 22(4), pp. 236–243, 1994.

* cited by examiner

Primary Examiner—Thurman K. Page
Assistant Examiner—Humera N. Sheikh
(74) Attorney, Agent, or Firm—Hesna J. Pfeiffer

(57) ABSTRACT

Agglomerates of β-lactam antibiotics, such as penicilllin V potassium, amoxicillin trihydrate, cephalexin monohydrate, which are suitable for direct tablet formation.

6 Claims, No Drawings

AGGLOMERATES OF β-LACTAM ANTIBIOTICS AND PROCESSESS FOR MAKING AGGLOMERATES

This application is a 371 of PCT/EP97/01269, filed Mar. 13, 1997.

This invention relates to agglomerates of β-lactam antibiotics, including e.g. penicillin V potassium, amoxicillin trihydrate, cephalexin monohydrate, which are suitable for direct tablet formation.

The most important and most frequently used form for orally administrable β-lactam antibiotics and mixtures, containing β-lactam antibiotics beside a second pharmaceutically active agent and optionally beside auxiliaries, is a tablet or a film tablet. For the production of a tablet or a film tablet, there are at the moment two processes known, namely granulation and direct tablet formation.

During granulation, generally very fine-grained, powdered, cohesive, non free-flowing and non-compressible pharmaceutically active agents are granulated in a multi-stage process to form coarser, free-flowing and compressible granules. In such a process, the pharmaceutically active agents are mixed in a first step with a binding agent, compacted whilst moist or dry and subsequently granulated in a second step through a sieve. The binding agent may, e.g. be dissolved in the moistening liquid used for moistening and granulating the powder. In a moist granulation process, drying of the granules is carried out including subsequent sieving to the final grain size. In a dry granulation process, after granulation it is generally necessary to separate the particles which are too coarse or too fine, and to recycle these particles, the coarse grain particles being pulverized again and the fine particles being compacted again. The granulates obtained may be mixed with auxiliaries which are preferably pharmaceutically acceptable required for tablet formation and compressed into tablets.

Granulation is generally very time and energy consuming and expensive, and may be thus extremely uneconomical. The described production processes for a tablet requires a considerable amount of apparatus and a high amount of validation work, and owing to the large number of production steps there are many sources of error.

Direct tablet formation is a much easier process; the pharmaceutically active agents being easily mixed with auxiliaries (carriers, binding agents, lubricants etc.) and the mixture is pressed into tablets. However, until now, despite the clear economic advantages over granulation, direct tablet formation could only be used to a limited extent, since it may generally only be carried out with, e.g. the following provisos: The pharmaceutically active agents has to be sufficiently free-flowing and compressible per se, and the proportion of pharmaceutically active agents per tablet must be a maximum of 100 mg or 25%. With such provisos good free-flow capability and good compressibility may only be obtained by addition of high amounts of special auxiliaries (e.g. Tablettose®, Ludipress® etc.).

In the case of β-lactam antibiotic tablets, the proportion of the β-lactam antibiotic per tablet may be up to 80% and more (e.g. 1 g and more), and β-lactam antibiotics are generally not sufficiently free-flowing and compressible per se. For example, especially penicillin V potassium, phenoxymethylpenicillin potassium, amoxicillin trihydrate and cephalexin monohydrate are generally obtained during production in an average volume-based grain size of 10 μm to 30 μm with the following grain size distribution:

| 4 μm to 80 μm | 80% |
|---|---|
| >125 μm | 1% to 5% | and having a bulk density of 0.15 g/ml to 0.45 g/ml.

These characteristics make it generally impossible to use the direct tablet formation process for β-lactam antibiotics.

Mixtures containing β-lactam antibiotics, for example a combination of amoxycillin trihydrate (β-lactam antibiotic) as, e.g. an anti-bacterially active compound with a second pharmaceutically active agent, e.g. a potassium salt of clavulanic acid (potassium clavulanate) as, e.g. a β-lactamase inhibitor are of enormous interest for the treatment of infections caused by gram-positive and gram-negative bacteria, which have become resistant to amoxycillin as a result of β-lactamase formation. Combinations of amoxicillin trihydrate/potassium clavulanate/auxiliaries are on the market under the trade name Augmentin®. The most important pharmaceutical form for the oral administration thereof is a tablet or a film tablet. Up to now, the preparation of Augmentin® tablets or film tablets has been particularly difficult because of the following problems in addition to the problems with tablet formation in case of β-lactam antibiotics as described above:

A potassium clavulanate may be extremely moisture sensitive and may degrade quickly in the presence of water A mixture of two pharmaceutically active agents in a defined ratio has to be produced which may include the danger of disintegration of the two components during production because, e.g. of inhomogeneous contents of a pharmaceutically active agent in a tablet or a film tablet The total proportion of the two pharmaceutically active agents per tablet may be up to 80% and more and the ability of the active ingredients to be compressed into a tablet or a film tablet may be determined almost exclusively by the physical properties of the active ingredients, i.e. deformation behaviour under pressure.

Thus, when producing a tablet or a film tablet with a combination of amoxicillin trihydrate and potassium clavulanate in a first step granulation has generally to be carried out, in order to ensure that a compressable mixture with satisfactory free-flow capability and compressibility is obtained; and to prevent disintegration of the active ingredients. However, owing to the extreme sensitivity of potassium clavulanate towards moisture, moist granulation with aqueous-alcoholic mixtures or binding agent solutions; or with pure water; which is at present the usual way for the production of β-lactam antibiotic tablets or film tablets, cannot be effected; because during moistening and subsequent granulation of the amoxycillin trihydrate/potassium clavulanate/auxiliaries powder, as well as during the subsequent drying of the granules, potassium clavulanate may be degraded due to the water present to an unacceptable extent.

In practice, up to now for the production of tablets or film tablets containing amoxicillin trihydrate and potassium clavulanate with sufficient uniformity there are in general only two alternative granulation processe, both of which may be complicated, and extremely uneconomical and unecological, namely:

Moist Granulation With Water-free Organic Solvents

The active ingredients amoxicillin trihydrate and potassium clavulanate are mixed in a first step with a binding agent, the mixture is moistened with a water-free, organic solvent, granulated and dried. The binding agent may also be added dissolved in the solvent. The granulates obtained may be sieved to the final grain size and mixed with tablet forming auxiliaries (binding agents, disintegrants etc.) before being compressed into tablets. Such a process is uneconomical and unecological, since the solvent has to be recycled; special equipment is necessary, solvent losses arise, etc.

Dry Granulation (Compactation, Briquette Formation)

The active ingredients amoxycillin trihydrate and potassium clavulanate may generally be mixed with a binding agent and compacted in dry form. Compactation may take place by compressing the pharmaceutically active agent/binding agent-mixture either on a roller compactor to form so-called "shells" or on a tablet press having large stamps to form so-called "briquettes". Both the shells and the briquettes obtained are pulverized or broken in a mill or a sieve, in order to obtain an appropriate granulate. After granulation it is generally necessary to separate the particles which are too coarse or too fine, and to recycle these particles, the coarse grain particles being pulverized again and the fine particles being compacted again (briquette formation). The granulates thus obtained may be mixed with auxiliaries required for tablet formation (lubricants, disintegrants etc.) which are preferably pharmaceutically acceptable and the mixture may be compressed to form tablets. Parts of the lubricants or disintegrants may be incorporated (mixed with active ingredient) prior to compacting/briquette formation.

Such a dry granulation production process may be unfavourable because it is very time-consuming it is expensive losses of active ingredient may be practically unavoidable it may require a considerable number of apparatus a high amount of pre-validation work is necessary a large number of production steps may be necessary there are a considerable amount of error sources.

Despite of such disadvantages, such a process is to be used for the production of amoxycillin trihydrate/potassium clavulanate film tablets owing obviously to the absence of alternative possibilities (see e.g. PCT application WO 95/28927).

We have surprisingly found agglomerates of β-lactams, including penicillin V potassium, amoxycillin trihydrate, cephalexin monohydrate which are free from auxiliaries and which have an excellent flowability, and which may be compressed directly into tablets optionally after mixing these agglomerates with auxiliaries; and a process for the production of free-flowing and auxiliary-free compressible β-lactam antibiotic agglomerates from powders.

We have also surprisingly found a mixture of pharmaceutically active agents including at least one β-lactam antibiotic, such as a mixture of amoxycillin trihydrate and potassium clavulanate, containing optionally auxiliaries, suitable for the production of a tablet (or a film tablet) by direct tablet formation; and a process for direct tablet formation of a mixture of pharmaceutically active agents including at least one β-lactam antibiotic, such as a mixture of amoxycillin trihydrate and potassium clavulanate, containing optionally auxiliaries which are pharmaceutically acceptable, avoiding moisturing of the mixture in fewer production steps than according to prior art processes.

Auxiliary-free agglomerates of a β-lactam antibiotic are new and forms part of the present invention.

Auxiliary-free agglomerates of a β-lactam antibiotic which have an excellent flowability, and which may be compressed directly into tablets optionally after mixing with auxiliaries may be e.g. such, of an average volume-based grain size of 200 μm to 1000 μm, preferably 400 μm to 600 μm. The distribution of grain size may be as follows:

| | |
|---|---|
| <100 μm: | 1% to 30%, for example 5% to 20% |
| 100–500 μm: | 10% to 80%, for example 20% to 60% |
| 500–1000 μm: | 10% to 80%, for example 25% to 60% |
| >1000 μm: | max. 30%, for example max. 15% |
| >2000 μm: | max. 0.5%, for example max. 0.1%. |

The bulk density of the agglomerates may, for example, be in the range of about 0.4 g/ml to about 0.8 g/ml, e.g. 0.4 g/ml to 0.8 g/ml; such as about 0.5 g/ml to about 0.7 g/ml, e.g. 0.5 g/ml to 0.7 g/ml.

The present invention provides therefore in one aspect auxiliary-free agglomerates of β-lactam antibiotics; especially of penicillin V potassium, amoxycillin trihydrate and cephalexin monohydrate; having for example an average volume-based grain size of 100 μm to 1000 μm, preferably 400 μm to 600 μm, such as 200 m to 600 μm; having for example the following distribution of grain size:

| | |
|---|---|
| <100 μm: | 1% to 30%, for example 5% to 20% |
| 100 μm to 500 μm: | 10% to 80%, for example 20% to 60% |
| 500 μm to 1000 μm: | 10% to 80%, for example 25% to 60% |
| >1000 μm: | max. 30%, for example max. 15% |
| >2000 μm: | max. 0.5%, for example max. 0.1%; | and/or having a bulk density of 0.4 g/ml to 0.8 g/ml, for example 0.5 g/ml to 0.7 g/ml.

Auxiliary-free agglomerates according to the invention may be produced as follows: A solid β-lactam antibiotic, e.g. penicillin V potassium, amoxycillin trihydrate and cephalexin monohydrate, e.g. in form of a powder, with an average volume-based grain size of 10 μm to 30 μm, with about the following distribution of grain size:

| | |
|---|---|
| 4 μm to 80 μm | 80% |
| >125 μm | 1 to 5% | and a bulk density of 0.15 g/ml to 0.45 g/ml, as usually obtained in the production process for a β-lactam antibiotic, may be formed into a paste, for example by conventional methods, with a liquid in which the β-lactam antibiotic is insoluble or slightly soluble. This paste may be kneaded and extruded in a double-screwed extruder having a specific mechanical energy input of 0.01 to 0.1 kilowatt-hour/kg, preferably of 0.02 to 0.6 kilowatt-hour/kg.

During the kneading procedure the temperature of the paste may be maintained in a range of about 10° C. to about 80° C., e.g. 10° C. to 80° C. Auxiliary-free agglomerates may be obtained which may be dried, e.g. as conventional, for example in a fluidized bed drier.

In another aspect the present invention provides a process for the production of auxiliary-free agglomerates of a β-lactam antibiotic, by the following steps a) forming a paste from a β-lactam antibiotic with a liquid, b) kneading the paste at a temperature of 10° C. to 80° C., c) extruding the paste in a double-screwed extruder having for example a specific mechanical energy input of 0.01 to 0.1 kilowatt-hour/kg, and, if desired, d) drying the agglomerates obtained.

The β-lactam, e.g. in form of a powder, may be placed into the extruder in an already moist form, or in dry form. If the β-lactam antibiotic, for example in form of a powder, is placed into the extruder in dry form the liquid may be dispersed into the extruder simultaneously with the β-lactam antibiotic.

Appropriate liquids include e.g. water, alcohols and mixtures thereof; as well as organic solvents such as acetone. An alcohol may preferably be ethanol or isopropanol.

The amount of liquids may be appropriate to result in a kneadable paste with the β-lactam antibiotic and may be preferably as follows (expressed in % by weight, based on the paste):

about 3 to about 20, e.g. 3 to 20, preferably about 5 to about 10, e.g. 5 to 10 for the case that the active ingredient is slightly dissolved by the liquid; and about 5 to about 35, e.g. 5 to 35, preferably about 10 to about 20, e.g. 10 to 20 for the case that the active ingredient is insoluble in the liquid.

The optimum degree of density of the β-lactam antibiotic agglomerates may be such that mechanical stability of the agglomerates is appropriate, i.e. after drying, the agglomerates should not disintegrate into a powder because this would negatively affect the free-flow capability. But the agglomerates should not be extremely mechanical stable (density too high), because during the tablet formation process such extreme stable agglomerates would not be prone to form mechanically stable tablets which thus could not be produced.

Surprisingly, the optimum degree of density in a process according to the present invention corresponds exactly to the observed maximum torque pick-up on the extrusion screw which passes through during extrusion as the amount of liquid increases. Thus, the optimum degree of density of the powder is very easily controllable.

The β-lactam agglomerates according to the present invention may be compressed, optionally after mixing with auxiliaries which are preferably pharmaceutically acceptable, such as polyvinyl pyrrolidone, talcum, magnesium stearate; directly into tablets of high unit weight, satisfactory mechanical stability and rapid release of of the β-lactam antibiotic (active ingredient). Since no binding agent and no bindings between the particles of active ingredient and a binding agent are generally present in the agglomerates as are generally present in moist granulation processes, the release of active ingredient from the directly compressed tablets according to the present invention may be considerably faster than from tablets produced by granulation as usual.

Compared with tablets produced by the multi-stage moist granulation process as described above , the tablets produced according to the present invention by direct tablet formation of the new-type agglomerates of active ingredient have, e.g. the following advantages:

Owing to the excellent free-flow capability of the agglomerates according to the present invention, the weight deviation of the tablets is less. The optimum degree of density of the agglomerates results in high mechanical stability (higher degree of hardness, lower friability), and, despite of this, the release of the pharmaceutically active agent, i.e. of the β-lactam antibiotic, from the tablet is considerably quicker.

A mixture of a β-lactam antibiotic such as amoxicillin trihydrate with a second pharmaceutically active agent, e.g. potassium clavulanate, may easily be produced by mixing agglomerates of a β-lactam antibiotic, e.g. of amoxicillin trihydrate, which are sufficiently free-flowing and compressible, such as agglomerates obtainable by the process of the present invention, with a second pharmaceutically active agent, which may be generally insufficiently free-flowing and incompressible, such as, e.g. potassium clavulanate having for example a grain size of ca. 5 μm to 100 μm which may be a normal grain size in pharmaceutical powders, obtained during production. We have surprisingly found that the mixture is sufficiently free-flowing and compressible for direct tablet formation even if a high degree of potassium clavulanate is mixed with the β-lactam antibiotic agglomerates according to the present invention.

The weight ratio of agglomerats of a β-lactam antibiotic, such as amoxycillin trihydrate and potassium clavulanate in the directly compressable mixture may be in the range of 12:1 to 1:1; e.g. 7:1 to 1:1; such as 4:1 to 1:1; for example 2:1 to 1:1.

Mixing of the β-lactam antibiotic agglomerates with a second pharmaceutically active agent, e.g. potassium clavulanate, e.g. in form of a powder, may be effected, e.g. in a forced-flow or free-fall mixer. Agglomerates of a β-lactam antibiotic according to the present invention, e.g. agglomerates of amoxycillin trihydrate may function as a carrier for for the second pharmaceuticalle active agent, e.g. potassium clavulanate, e.g. in form of a powder.

Auxiliaries, which are preferably pharmaceutically acceptable, for example auxiliaries conventional in tablet formation processes, such as for example lubricants, e.g. magnesium stearate; mold-separating agents, e.g. talcum; binding or filling agents, e.g. polyvinyl pyrrolidone, microcrystalline cellulose (Avicel), modified starch (Starch 1500 J); disintegrating agents, e.g. crosslinked carboxymethyl cellulose (Ac—Di—Sol), crosslinked carboxymethyl starch (Primojel) or crosslinked polyvinyl pyrrolidone (PVPP); may be present in the mixture of β-lactam antibiotic agglomerates and potassium clavulanate powder, preferably in small amounts because it was found that only small amounts may be necessary. Auxiliaries, optionally pre-dried, may be mixed into the mixture, for example before, during or after mixing of the β-lactam antibiotic agglomerates with potassium clavulanate powder.

The water activity of a mixture is described in literature and is generally described to be in the range of 0.2 to 0.6 (optimum 0.4). It has been found surprisingly that the compressability of the mixture according to the present invention is excellent even with substantially low water activity of the mixture, namely <0.2, which is a great advantage owing to the moisture sensitivity of e.g. potassium clavulanate. The water activity at 25° C. of a amoxycillin trihydrate/potassium clavulanate mixture according to the present invention may be <0.1, preferably <0.05.

Mixtures of agglomerates of a β-lactam antibiotic such as amoxicillin trihydrate with a second pharmaceutically active agent, e.g. potassium clavulanate, include particular preferred ranges in respect with average grain size and distribution of grain size, namely:

Average grain size of 100 μm to 800 μm, preferably 200 to 600 μm, with the following distribution of grain size:

| | |
|---|---|
| <100 μm: | 1% to 50%, preferably 10% to 50% |
| 100 μm to 500 m: | 20% to 90%, preferably 30% to 70% |
| 500 μm to 1000 μm: | 20% to 70%, preferably 10% to 50% |
| >1000 μm: | max. 15%, preferably max. 10% |
| >2000 μm: | max. 0.1%, preferably max. 0.1%. |

The bulk density of the mixture may, for example, be in the range of about 0.3 g/ml to about 0.8 g/ml, e.g. 0.3 g/ml to 0.8 g/ml; such as about 0.4 g/ml to about 0.6 g/ml; e.g. 0.4 g/ml to 0.6 g/ml. The angle of respose of the mixture which is a measure for flowability may be, e.g. <40°, preferably <35°.

Such mixtures are new and form also part of the present invention.

In another aspect the present invention provides a mixture of agglomerates of an active β-lactam, e.g. amoxycillin trihydrate, for example having an average grain size of 100 μm to 800 μm, for example 200 μm to 600 μm; and a second active ingredient, e.g. a potassium salt of clavulanic acid, e.g. in form of a powder;

with or without auxiliaries;

the mixture having, for example, the following distribution of grain size:

| | |
|---|---|
| <100 μm: | 1% to 50%, preferably 10% to 50%, |
| 100–500 μm: | 20% to 90%, preferably 30% to 70%, |
| 500–1000 μm: | 20% to 70%, preferably 10% to 50%, |
| >1000 μm: | max. 15%, preferably max. 10%, |
| >2000 μm: | max. 0.1%, preferably max. 0.1%; | the mixture having for example a bulk density of 0.3 g/ml to 0.8 g/ml, preferably 0.4 g/ml to 0.6 g/ml for example an angel of repose of <40°, preferably <35°.

Mixtures of agglomerates of a β-lactam antibiotic, for example amoxycillin trihydrate and a second pharmaceutically active agent, e.g. potassium clavulanate in form of a powder according to the present invention, containing optionally auxiliaries, may be directly compressed into tablets with high uniformity of the content of active ingredients and high uniformity of tablet weight, satisfactory mechanical stability and rapid release of active ingredient. Since no moisture is necessary in the entire production process of the tablets, potassium clavulanate is not degraded due to moisture effects which in addition ensures high stability of potassium clavulanate in the finished pharmaceutical preparation.

In another aspect, the present invention provides the use of auxiliary-free β-lactam antibiotic agglomerates in the production of a mixture of a β-lactam antibiotic; and a second pharmaceutically active agent, with or without auxiliaries, having for example an average grain size of 100 μm to 800 μm; and in a further aspect Auxiliary-free agglomerates of β-lactam antibiotics, especially of phenoxymethylpenicillin potassium, amoxycillin trihydrate and cephalexin monohydrate, which is suitable for direct tablet formation, characterised in that the agglomerates have an average volume-based grain size of 200–1000 μm, preferably 400–600 μm, with the following distribution of grain size:

| | |
|---|---|
| <100 μm: | 1–30%, |
| 100–500 μm: | 10–80%, |
| 500–1000 μm: | 10–80%, |
| >1000 μm: | max. 30%, |
| >2000 μm: | max. 0.5%, | and a bulk density of 0.4 to 0.8 g/ml; and in another aspect

A mixture suitable for direct tablet formation, which contains amoxycillin trihydrate and the potassium salt of clavulanic acid as the essential components, characterized in that amoxycillin trihydrate is present in the form of an agglomerate and the mixture has an average grain size of 100–800 μm, preferably 200–600 μm, with the following distribution of grain size:

| | |
|---|---|
| <100 μm: | 1–50%, preferably 10–50%, |
| 100–500 μm: | 20–90%, preferably 30–70%, |
| 500–1000 μm: | 20–70%, preferably 10–50%, |
| >1000 μm: | max. 15, preferably max. 10, |
| >2000 μm: | max. 0.1, | and having a bulk density of 0.3 g/ml–0.8 g/ml, preferably 0.4 g/ml–0.6 g/ml, and an angle of repose of <40°, preferably <35°.

Tablets produced by compression of a mixture of agglomerates of a β-lactam antibiotic, such as e.g. amoxycillin trihydrate with a second pharmaceutically active agent, e.g. potassium clavulanate and optionally with auxiliaries, may also be film-coated with film suspensions, dispersions (aqueous or organic solvents) in coating apparatus (drum, fluidized bed), for example as conventional.

Tablets, e.g. for oral administration comprising compressed agglomerates of a β-lactam antibiotic, such as e.g. penicillin V potassium, amoxycillin trihydrate, cephalexin monohydrate optionally in mixture with pharmaceutically acceptable auxiliaries are new and form also part of the present invention.

In a further aspect the present invention provides a tablet for e.g. oral administration comprising compressed agglomerates of a β-lactam antibiotic optionally in mixture with pharmaceutically acceptable auxiliaries.

Tablets, e.g. for oral administration, comprising compressed agglomerates of a β-lactam antibiotic, such as e.g. amoxicillin trihydrate in mixture with a second pharmaceutically active agent, e.g. potassium clavulanate and optionally with pharmaceutically acceptable auxiliaries are new and form also part of the present invention.

In a further aspect the present invention provides a tablet, e.g. for oral administration comprising compressed agglomerates of a β-lactam antibiotic, such as e.g. amoxicillin trihydrate in mixture with a second pharmaceutically active agent, e.g. potassium clavulanate and with or without pharmaceutically acceptable auxiliaries.

The following example illustrate the invention. All temperatures are given in degree Celsius.

EXAMPLE 1

Production of Agglomerates of Phenoxymethylpenicillin Potassium (Penicillin V Potassium)

Isopropanol-moist penicillin V potassium (10% to 20% isopropanol based on moist mass) is agglomerated in a double-screwed extruder (process length 4 D) at 100 kg/h at a maximum torque pick-up of the extrusion screws of 25% to 30%. The screws are configured with conveyer elements, and right- and left-handed kneading blocks. After drying the extruded moist mass in a fluidized bed drier, agglomerates of penicillin V potassium (yield 99.7% of theory) having the following properties are obtained:

Distribution of grain size:

| Distribution of grain size: | |
|---|---|
| <100 μm: | 12% |
| 100 μm to 500 μm: | 68% |
| 500 μm to 1000 μm: | 18% |
| >1000 μm: | 2% |

Bulk density: 0.58 g/ml; stamped density: 0.70 g/ml.

EXAMPLE 2
Production of Agglomerates of Phenoxymethylpenicillin Potassium (Penicillin V Potassium)

Dry, powdered penicillin V potassium (BP, USP) is agglomerated in a double-screwed extruder (process length 3 D) with water (5% to 10% based on moist mass) at 200 kg/h at a maximum torque pick-up of the extrusion screws of 10% to 15%. The screws are configured with conveyer elements and right-handed kneading blocks. After drying the extruded moist mass in a fluidized bed drier, agglomerates of penicillin V potassium (yield 99.8%) having the following properties are obtained:

Distribution of grain size:

| Distribution of grain size: | |
|---|---|
| <100 μm: | 10% |
| 100 μm to 500 μm: | 39% |
| 500 μm to 1000 μm: | 52% |
| >1000 μm: | 1%. |

Bulk density: 0.63 g/ml; stamped density: 0.71 g/ml.

EXAMPLE 3
Production of Agglomerates Amoxicillin Trihydrate

Acetone-moist amoxicillin trihydrate (10% to 15% acetone based on moist mass) is agglomerated in a double-screwed extruder (process length 3 D) at 150 kg/h at a maximum torque pick-up of the extrusion screws of 25% to 35%. The screws are configured with conveyer elements and right- and left-handed kneading blocks. After drying the extruded moist mass in a fluidized bed drier, agglomerates of amoxicillin trihydrate (yield 99.9%) having the following properties are obtained:

Distribution of grain size:

| Distribution of grain size: | |
|---|---|
| <100 μm: | 13% |
| 100–500 μm: | 71% |
| 500–1000 μm: | 12% |
| >1000 μm: | 4% |

Bulk density: 0.56 g/ml; stamped density: 0.67 g/ml.

EXAMPLE 4
Production of Agglomerates of Cephalexin Monohydrate

Dry cephalexin monohydrate in form of a powder is agglomerated in a double-screwed extruder (process length 4 D) with 50% aqueous ethanol (5% to 15% based on moist mass) at 200 kg/h at a maximum torque pick-up of the extrusion screws of 12% to 18%. The screws are configured with conveyer elements and right-handed kneading blocks.

After drying the extruded moist mass in a fluidized bed drier, agglomerates of cephalexin monohydrate (yield 99.7%) having the following properties are obtained:

Distribution of grain size:

| Distribution of grain size: | |
|---|---|
| <100 μm: | 7% |
| 100–500 μm: | 43% |
| 500–1000 μm: | 47% |
| >1000 μm: | 3%. |

Bulk density: 0.60 g/ml; stamped density: 0.71 g/ml.

EXAMPLE 5
Preparation of Tablets from Agglomerated Penicillin V Potassium

The tablet ingredients are as follows:

| | |
|---|---|
| Penicillin V potassium, agglomerated according to example 1 | 150.0 kg |
| Polyvinyl pyrrolidone K25 | 6.0 kg |
| Talcum | 6.9 kg |
| Polyethylene glycol 6000 | 2.6 kg |
| Magnesium stearate | 2.2 kg |

The auxiliaries are sieved through a 1.0 mm sieve and subsequently mixed for ca. 10 minutes at 20 ram in a freefall mixer (200 liters, Rhonerad) with penicillin V potassium agglomerated according to example 1.

This mixture is compressed on a rotating press (KILLIAN LX 18) at a rate of 100,000 tablets per hour.

Average tablet weight: 705 mg

Relative standard deviation of weight; 0.5%

Hardness of the tablets (Pharmatest—breaking strength tester P58200): between 100 N and 130 N Friability (400 rpm, Roche Friabilator): 0.6%.

The tablets disintegrate in water at 37° C. within 6 minutes.

100% of the penicillin V-potassium in a tablet have dissolved after 15 minutes in a phosphate buffer pH 6.8 at 37° C. (Paddel model 50 rpm).

EXAMPLE 6
Preparation of Tablets From Agglomerated Amoxicillin Trihydrate

The tablet ingredients are as follows:

| | |
|---|---|
| Amoxicillin trihydrate, agglomerated according to example 3 | 172.2 kg |
| Polyvinyl pyrrolidone | 3.75 kg |
| Sodium carboxymethyl starch | 6.0 kg |
| Cellulose (micro-crystalline), pH 10.2 | 16.2 kg |
| Magnesium stearate | 1.5 kg |

The auxiliaries are sieved through a 1.0 mm sieve and subsequently mixed for ca. 10 minutes at 20 rpm in a freefall mixer (300 liters, Rhonerad) with amoxicillin trihydrate agglomerated as in example 3.

This mixture is compressed on a rotating press (KILLIAN LX 18) at a rate of 85,000 tablets per hour.

Average tablet weight: 665 mg

Relative standard deviation of weight: 0.4%

Hardness of the tablets (determined as in example 5): between 130 N and 160 N

Friability (determined as in example 5): 0.7% (400 revolutions).

The tablets disintegrate in water at 37° C. within 3 minutes, and, after 20 minutes, 100% of the amoxicillin trihydrate in the tablet have dissolved.

EXAMPLE 7

Mixture of Agglomerated Amoxycillin Trihydrate and Clavulanic Acid in Form of a Potassium Salt Total mixture: 4 kg.
Amoxycillin trihydrate was agglomerated according to examples 1 to 4.

| Composition (% w/w) | |
|---|---|
| Agglomerated amoxycillin trihydrate, (calculated as water-free in form of the free acid) | 77 (+/−10) |
| Clavulanic acid in form of the potassium salt, (calculated as the free acid) | 33 (+/−10) |

Amoxicillin trihydrate agglomerates and potassium clavulanate are mixed for 10 minutes at 20 rpm in a dry atmosphere in a free-fall mixer (Rhoenrad, 10 liter milling drum); the average grain size of the mixture being 320 μm.

Distribution of grain size:

| Distribution of grain size: | |
|---|---|
| <100 μm | 34% |
| 100 μm to 500 μm | 50% |
| 500 μm to 1000 μm | 13% |
| >1000 μm | 3% |
| >2000 μm | 0% |

Bulk density: 0.43 g/ml.
The mixture is free-flowing.
Angle of respose (Pfrengle determination method): 34±2°
Water activity (see for example P. H. Stahl, Feuchtigkeit und Trocknen in der pharmazeutischen Technologie, UTB Steinkopff): <0.1 at 25° C.

EXAMPLE 8

Mixture of Agglomerated Amoxycillin Trihydrate and Clavulanic Acid in Form of a Potassium Salt Total mixture: 5 kg.
Amoxycillin trihydrate was agglomerated according to examples 1 to 4.

| Composition (% w/w) | |
|---|---|
| Agglomerated amoxycillin trihydrate, (calculated as water-free in form of the free acid) | 80 (+/−10) |
| Clavulanic acid in form of the potassium salt, (calculated as the free acid) | 20 (+/−10) |

Amoxicillin trihydrate agglomerates and potassium clavulanate are mixed for 3 minutes at 90 rpm in a dry atmosphere in a forced-flow mixer (Stephan UHC 15 liters); the average grain size of the mixture being 340 μm.

Distribution of grain size:

| Distribution of grain size: | |
|---|---|
| <100 μm | 26% |
| 100 μm to 500 μm | 51% |
| 500 μm to 1000 μm | 14% |
| >1000 μm | 9% |
| >2000 μm | 0% |

Bulk density: 0.54 g/ml.
The mixture is free-flowing.
Angle of respose (Pfrengle determination method): 32±2°
Water activity (see for example P. H. Stahl, Feuchtigkeit und Trocknen in der pharmazeutischen Technologie, UTB Steinkopff): <0.1 at 25° C.

EXAMPLE 9

Mixture of Agglomerated Amoxycillin Trihydrate and Clavulanic Acid in Form of a Potassium Salt Total mixture: 5 kg.
Amoxycillin trihydrate was agglomerated according to examples 1 to 4.

| Composition (% w/w) | |
|---|---|
| Agglomerated amoxycillin trihydrate, (calculated as water-free in form of the free acid) | 87.5 (+/−10) |
| Clavulanic acid in form of the potassium salt, (calculated as the free acid) | 12.5 (+/−10) |

Amoxicillin trihydrate agglomerates and potassium clavulanate are mixed for 10 minutes at 20 rpm in a dry atmosphere in a free fall mixer (Rhonerad, 10 liters milling drum); the average grain size of the mixture being 450 μm.

Distribution of grain size:

| Distribution of grain size: | |
|---|---|
| <100 μm | 14% |
| 100 μm to 500 μm | 46% |
| 500 μm to 1000 μm | 38% |
| >1000 μm | 12% |
| >2000 μm | 0% |

Bulk density: 0.61 g/ml.
The mixture is free-flowing.
Angle of respose (Pfrengle determination method): 31±2°
Water activity (see for example P. H. Stahl, Feuchtigkeit und Trocknen in der pharmazeutischen Technologie, UTB Steinkopff): <0.1 at 25° C.

EXAMPLE 10
Tablet of a Mixture of Agglomerated Amoxycillin Trihydrate and Clavulanic Acid in Form of a Potassium Salt

| Composition | |
|---|---|
| Agglomerated amoxycillin trihydrate, (calculated as water-free in form of the free acid) | (% w/w of total mixture weight) 77 (+/−10) |
| Clavulanic acid in form of the potassium salt, (calculated as the free acid) | (% w/w of total mixture weight) 33 (+/−10) |
| Polyvinyl pyrrolidine K25 (KOLLIDON 25 ®) | 0.15 kg |
| Talcum | 0.19 kg |
| Magnesium stearate | 0.12 kg |
| Crosscarmelose sodium (AcDiSol ®) | 0.20 kg |
| Cellulose micro-crystalline (AVICEL, pH 102) | 0.50 kg |

The auxiliaries are sieved through a 1.0 mm sieve and subsequently mixed under dry atmosphere for 10 minutes at 20 rpm in a freefall mixer (Rhonerad, 10 liters milling drum) with agglomerates of amoxicillin trihydrate and potassium clavulanate as obtained according to example 7.

This mixture is compressed on a rotating press (PHARMA 1) at a rate of 50,000 tablets per hour.

Average tablet weight: 635 mg

Relative standard deviation of weight: 0.4%

Hardness of the tablets (determined as in example 5): between 110 N and 142 N

Friability (determined as in example 5): 0.7% (400 revolutions).

The tablets disintegrate in water at 37° C. within 8.5 minutes, and after 30 minutes, 100% of the amoxicillin trihydrate and of the potassium clavulanate in the tablet have dissolved (Paddel model, water 37° C., 75 rpm).

Amoxycillin content per tablet (average of 20 tablets): 97 to 103% of theory

Clavulanic acid content per tablet (average of 20 tablets): 96 to 102% of theory This shows a high uniformity of content of the two active ingredients per tablet.

EXAMPLE 11
Tablet of a Mixture of Agglomerated Amoxycillin Trihydrate and Clavulanic Acid in Form of a Potassium Salt

| Composition | |
|---|---|
| Agglomerated amoxycillin trihydrate, (calculated as water-free in form of the free acid) | (% w/w of total mixture weight) 87.5 (+/−10) |
| Clavulanic acid in form of the potassium salt, (calculated as the free acid) | (% w/w of total mixture weight) 12.5 (+/−10) |
| Polyvinyl pyrrolidine K25 (KOLLIDON 25 ®) | 0.53 kg |
| Highly disperse silicon dioxide (AEROSIL 200 ®) | 0.18 kg |
| Magnesium stearate | 0.20 kg |
| Crosscarmelose sodium (AcDiSol ®) | 0.40 kg |
| Cellulose micro-crystalline (AVICEL, pH 101) | 1.20 kg |

The auxiliaries are sieved through a 1.0 mm sieve under dry atmosphere and subsequently mixed under dry atmosphere for 10 minutes at 20 rpm in a freefall mixer (Rhonerad, 15 liters milling drum) with agglomerates of amoxicillin trihydrate and potassium clavulanate as obtained according to example 9.

This mixture is pressed on a rotating tablet press (KILIAN Eifel RUH 3) at a rate of 80,000 tablets per hour.

Average tablet weight: 1065 mg

Relative standard deviation of weight: 0.76%

Hardness of the tablets (determined as in example 5): between 149 N and 178 N

Friability (determined as in example 5): 1.1% (400 revolutions).

The tablets disintegrate in water at 37° C. within 9.05 minutes, and after 30 minutes, more than 90% of the amoxicillin trihydrate and more than 90% of the potassium clavulanate in the tablet have dissolved (Paddel model, water 37° C., 75 rpm).

Amoxycillin content per tablet (average of 20 tablets): 96 to 102% of theory

Clavulanic acid content per tablet (average of 20 tablets): 95 to 103% of theory This shows a high uniformity of content of the two active ingredients per tablet.

What is claimed is:

1. Process for the production of agglomerates of a β-lactam antibiotic selected from penicillin V potassium, amoxicillin trihydrate or cephalexin monohydrate, wherein said agglomerates consist essentially of agglomerates between particles of said β-lactam, said process comprising the steps of a) forming a paste from said β-lactam antibiotic with a liquid, b) kneading the paste at a temperature of 10° C. to 80° C., c) extruding the paste in a double-screwed extruder, and d) drying the agglomerates obtained.

2. Agglomerates of β-lactam antibiotics selected from penicillin V potassium, amoxicillin trihydrate or cephalexin monohydrate, wherein said agglomerates consist essentially of agglomerates between particles of said β-lactam, suitable for direct tablet formation, characterised in that the agglomerates have an average volume-based grain size of 200–1000 μm, with the following distribution of grain size:

| <100 μm: | 1–30%, |
|---|---|
| 100–500 μm: | 10–80%, |
| 500–1000 μm: | 10–80%, |
| >1000 μm: | max. 30%, |
| >2000 μm: | max. 0.5%, | and a bulk density of 0.4 to 0.8 g/ml.

3. A mixture suitable for direct tablet formation, which contains amoxycillin trihydrate and the potassium salt of clavulanic acid as the essential components, characterized in that amoxycillin trihydrate is present in the form of an agglomerate consisting of agglomerates between particles of said amoxycillin trihydrate and the mixture has an average grain size of 100–800 μm, with the following distribution of grain size:

| <100 μm: | 1–50%, |
|---|---|
| 100–500 μm: | 20–90%, |
| 500–1000 μm: | 20–70%, |

-continued

| | |
|---|---|
| >1000 μm: | max. 15%, |
| >2000 μm: | max. 0.1%, | and a bulk density of 0.3 to 0.8 g/ml and an angle of repose of <40°.

4. A mixture according to claim 3, having an average grain size of 200–600 μm with the following distribution of grain size:

| | |
|---|---|
| 100 μm: | 10–50%, |
| 100–500 μm: | 30–70%, |

-continued

| | |
|---|---|
| 500–1000 μm: | 10–50%, |
| >1000 μm: | max. 10, |
| >2000 μm: | max. 0.1, | and having a bulk density of 0.4 g/ml–0.6 g/ml, and an angle of repose of <35°.

5. Agglomerates of claim 2, wherein the agglomerates have an average volume-based grain size of 400–600 μm.

6. Agglomerates of a β-lactam antibiotic selected from penicillin V potassium, amoxicillin trihydrate or cephalexin monohydrate produced according to the process of claim 1.

* * * * *